(12) United States Patent
Anderson et al.

(10) Patent No.: US 7,091,830 B2
(45) Date of Patent: Aug. 15, 2006

(54) SUBTERRANEAN TWO-WIRE POWER AND COMMUNICATIONS NETWORK

(75) Inventors: Scott K. Anderson, Meridian, ID (US); David J. Anderson, Meridian, ID (US)

(73) Assignee: Technical Development Consultants, Inc., Meridian, ID (US)

( * ) Notice: Subject to any disclaimer, the term of this patent is extended or adjusted under 35 U.S.C. 154(b) by 524 days.

(21) Appl. No.: 10/688,190

(22) Filed: Oct. 16, 2003

(65) Prior Publication Data

US 2004/0086053 A1 May 6, 2004

(51) Int. Cl.
*G05B 11/01* (2006.01)
(52) U.S. Cl. ................. 340/310.04; 370/479; 375/257; 137/78.3
(58) Field of Classification Search .......... 340/310.01, 340/310.04, 310.06; 137/78.3; 370/458, 370/479; 307/38; 375/257
See application file for complete search history.

(56) References Cited

U.S. PATENT DOCUMENTS

| 3,665,474 | A | * | 5/1972 | Thayer ....................... 375/286 |
| 3,689,886 | A | * | 9/1972 | Durkee .................. 340/825.26 |
| 4,200,862 | A | | 4/1980 | Campbell et al. |
| 4,300,126 | A | * | 11/1981 | Gajjar ......................... 307/17 |
| 4,328,482 | A | * | 5/1982 | Belcher et al. ........ 340/310.12 |
| 4,329,678 | A | * | 5/1982 | Hatfield ................. 340/310.12 |
| 4,528,667 | A | * | 7/1985 | Fruhauf ...................... 714/809 |
| 4,553,247 | A | * | 11/1985 | Harris ....................... 375/214 |
| 4,815,106 | A | * | 3/1989 | Propp et al. ................. 375/257 |
| 5,089,974 | A | | 2/1992 | Demeyer et al. |
| 5,491,463 | A | | 2/1996 | Sargeant et al. |
| 5,546,974 | A | * | 8/1996 | Bireley ...................... 137/78.3 |
| 5,614,811 | A | * | 3/1997 | Sagalovich et al. ......... 323/207 |
| 6,188,314 | B1 | * | 2/2001 | Wallace et al. ............. 340/438 |
| 6,657,443 | B1 | * | 12/2003 | Anderson ................... 324/664 |
| 6,747,463 | B1 | * | 6/2004 | Rynhart et al. ............. 324/664 |
| 6,798,215 | B1 | * | 9/2004 | DeHart ....................... 324/640 |
| 6,831,468 | B1 | * | 12/2004 | Anderson et al. ........... 324/664 |
| 2003/0097482 | A1 | | 5/2003 | DeHart et al. |

\* cited by examiner

*Primary Examiner*—Timothy Edwards, Jr.
(74) *Attorney, Agent, or Firm*—Your Intellectual Property Matters, Robert A. Frohwerk

(57) ABSTRACT

A combination of frequency and time division multiplexed signals communicates using bursts of higher frequency sinusoidal waves superimposed upon the alternating current in a two-wire power distribution network. A synchronization pattern precedes data, all bursts having the same frequency to overcome problems caused by varying reactances, and all bursts being confined within negative half-cycles of the AC power. Such networks minimize the amount of wire needed to connect large numbers of devices to a common controller while covering large distances, and requiring no particular connection pattern or terminations, whether near the surface, above ground, or in deep earth wells. In an irrigation system they accommodate at once solenoid valves and distributed environmental sensors. Landscape changes that would otherwise require new wiring to accommodate new irrigation zones are facilitated by merely tapping into the two-wire communications lines at the nearest accessible point. Outdoor lighting controls and security sensors are easily accommodated.

63 Claims, 5 Drawing Sheets

SUBTERRANEAN TWO-WIRE POWER AND COMMUNICATIONS NETWORK

CROSS-REFERENCES TO RELATED APPLICATIONS

Not Applicable

STATEMENT REGARDING FEDERALLY SPONSORED RESEARCH OR DEVELOPMENT

Not Applicable

SEQUENCE LISTING OR PROGRAM

Not Applicable

FIELD OF THE INVENTION

The present invention relates generally to systems wherein electronic communication signals are sent from one point to another by means of existing power lines, especially where the power lines are subterranean. The present invention relates specifically to communications carried on underground wiring within a sprinkler irrigation system.

BACKGROUND

Early remote control of electrical devices was accomplished through the use of radio frequency transmitters. Though these systems could address devices over a very large area, they were rather expensive, especially where several controllable devices were to be addressed. With advances in technology these transmitters have been reduced in size to pocket pagers and are still a common means of control, though their relatively high cost still limits their application. For less expensive control within smaller, more local regions, ultrasonic transmitters were used, as for home television sets, until these were largely replaced by infrared systems upon the advent of Light-Emitting Diodes.

Many systems exist where remote control is not required to be wireless. Utility companies within the power industry recognized that, with their vast array of long-line wired connections, wireless for them might not be necessary. In 1972 Paull (U.S. Pat. No. 3,656,112) taught one means of remotely reading utility meters. The power that supplied the circuitry to generate and transmit data when requested was drawn from the same power line that was being metered. However, Paull's application was limited to relatively local rather than long distance use since the transfer of data was still accomplished wirelessly by radio or acoustic signals, Remote control systems that were fully wired, as opposed to being wireless, continued to use separate cables to carry power and data. For systems that covered a large area, this presented considerable expense, both in the cost of material for extra data cables and the labor involved in their installation. The application of control signals, data signals and power all being transmitted along a single pair of conductors was yet to come.

About the same time as Paull was using wireless means to read information from power lines, Durkee in U.S. Pat. No. 3,689,886 used sets of receivers attached to a power line to remotely control individual devices with both power and control carried by the same two conductors. Each receiver was tuned for sensitivity to one particular frequency from among a set of frequencies. A receiver would enable its controlled device if its assigned frequency was detected within a pre-assigned time slot following zero-crossings of the alternating current (AC) power. The delay and duration of the time slots were established by one-shots which were set manually. If the required frequency was not present within the prescribed window, the device controlled by the receiver would be disabled. This approach allowed for activation of only one device code at a time since the coded frequency had to be repeated on each cycle of the AC power in order to keep a device enabled.

To allow more than one device to be independently enabled at any given time, Sherwin described his "Frequency Selective Remote Control System" in U.S. Pat. No. 3,729,710 (1973). It used the two-wire power line to carry enabling signals to each of a set of remote devices. A set of discrete frequencies within the band of 10 kHz to 35 kHz were superimposed on the power line, each device's receiver being tuned to a specific frequency. By sequentially scanning multiple frequencies onto the power line, for say 10 msec each, more than one device could be activated within any particular period of time. Once enabled, a receiver would hold its controlled device in the enabled state long enough to allow the transmitter to scan all of the devices in the system before allowing the device to drop out for lack of freshly updated enabling input.

So far these were essentially analog systems where control capabilities were limited to two states, the controlled devices being either On or Off. Fowler (U.S. Pat. No. 4,093,946) in 1976 was among the first to describe a method that was more generally capable of communicating data over a two-wire power system. He taught how a current source could be used to superimpose pulses representing a binary signal onto a low impedance power line. However, the data carried by Fowler's system was limited to small numeric values. There was no encoding involved. Addresses of controlled devices and the data that they returned in response to their being selected was simply a count of pulses that occurred within a transmission window. The power supplied was DC (direct current) that was stored in a capacitor at each controller in order to carry it through what might be considered blackout periods during which the power line was shorted out in order to transmit data.

U.S. Pat. No. 4,200,862 assigned to Pico Electronics Limited of Fife, Scotland in 1980 by Campbell, et al. may have been the first to transmit control and data over a two-wire power line. The protocol described by Campbell, et al. has now become pervasive. Commonly known as the X-10 interface, a de facto standard, the home automation industry has grown up around this particular technology that was enhanced by Thompson's U.S. Pat. No. 4,628,440 and again by Campbell in U.S. Pat. No. 4,638,299 over the next few years.

Though the X-10 system allows selection of devices by binary codes up to 255, it is still somewhat limited in control and data capabilities. Initially X-10 controllers were limited to the On or Off states of previous designs with the additional capability of sending a "Dim" signal to lamps.

In the 1996 U.S. Pat. No. 5,491,463 issued to Sargeant, et al., mention is made of the allowance in the X-10 protocol for a reserved byte code to indicate an extension for transmission of a data stream. A special code was to be followed immediately by a series of 8-bit bytes with the first 8-bit byte identifying the number of data bytes to follow. However, at that time Sargeant, et al. were not aware of any commercially available product in which that feature had been implemented, and so they proceeded to describe how to do so.

Advances in the above-described technologies have continued, but with the emphasis being on automation within the home or other interior'spaces such as offices and hotels. The X-10 protocol with its use of 120 kHz signaling does not seem to have migrated well to the outdoors where the reactances and line lengths encountered are not suitable for binary data transmissions. Even the X-10's attempt to overcome noise by transmitting code patterns twice, first in their true form followed by a second copy in complementary form, has been insufficient to adapt the system for use in the less predictable outdoor and underground environments. Meanwhile, other techniques have developed for outdoor use, but there do not seem to be any standards, and no technique is nearly as pervasive as the X-10 is indoors.

Control of turf irrigation systems presents a frequent, if not the most common, requirement for outdoor automation. Several two-wire power and communications networks have been developed for underground turf irrigation systems. Their purpose is to reduce the amount of copper wire needed to install the system and to facilitate landscape upgrades and wiring repairs. Typically these have been developed with an emphasis on the communications means, many of them being wireless, and have overlooked the utility of using 24 Volts AC as the power option for the solenoid valves and other devices on the network. The departure from the commonly available, and therefore relatively inexpensive, 24 Volt AC components has necessitated the use of special valves operating at higher voltages or the need to generate a valve power signal that simulates 24 Volts AC, the latter alternative in some cases being at the expense of reliable valve response.

Some of the two-wire systems described above and their more recent enhancements have employed binary communications signals superimposed on the power network. Binary signals require that the two-wire bus be well-managed. That is, it may be required that the two-wire pair be twisted or that the conductors remain in close proximity to one another or that they must run from device to device with terminations and repeaters at each node. Without such control of line quality, reflections from the ends of the lines add signal artifacts, such as 'porches', to the ends of the binary signals. Poorly managed reactances cause distortion of digital signals in general, and the two-wire networks treated here are particularly susceptible.

A further limitation of two-wire systems based on the communication of binary signals is the result of noise spikes from the environment masquerading as data signals. Such broadband spikes easily disrupt the communication of binary signals leading to errors and the necessity for repeated transmissions at the expense of data rates. The disclosed invention deals with these issues from the basis of a scheme that combines Time Division Multiplex and Frequency Division Multiplex methods. The combination maintains the advantages of each method, achieving extremely low error rates while using simple hardware supported by sophisticated though relatively inexpensive microcontroller code.

BRIEF SUMMARY OF THE INVENTION

The present invention utilizes two wires to convey 24 Volts AC throughout the underground network. The 24 Volts AC is delivered to the two-wire network through an inductor from a transformer. Superimposed on the 24 Volt AC power signal is a high frequency sinusoidal carrier signal that is transmitted in bursts representing data bits. Since these bursts are monotonic, that is, of a single sinusoidal frequency, they are not distorted by reactances of the two-wire line and its unterminated line ends. They are merely reduced in amplitude and shifted in phase, neither of which impacts reliable transmission. Paired wiring is not needed, and, in fact, one side of the two-wire system may be much longer than the other. Multiple star connections are easily accommodated without signal distortion. Each high frequency burst lasts for a sufficient number of cycles so as to use, a microcontroller-based digital bandpass filter for detection and thus provide a high measure of redundancy and associated improvement in signal-to-noise ratio.

The high-frequency sinusoidal bursts are transmitted in eight time slots. The presence of a burst in a slot is interpreted as a logical '1' and the absence of a burst as a logical '0'. The group of eight time slots and associated bursts is one data byte.

The data bytes are transmitted only during the negative half-cycle of the 24 Volt AC waveform. Only one byte is transmitted during each negative half cycle. Devices attached to the line are restricted from capacitively loading the line during the negative half-cycle, whereas inductive loads may be applied during both half cycles. Thus all devices rectifying power onto a storage capacitor are restricted to half-wave rectification using the positive half-cycle.

Synchronization of the burst positions and data byte occurrences is achieved by setting up a virtual clock in each device at the beginning of a communications sequence. All devices communicating on the network have such a clock. Each clock responds to a special synchronization pattern that is transmitted just prior to the beginning of data transmission. By establishing a reference in response to that pattern, each device is able to precisely time the occurrence of each data bit and byte as the data arrives and to reconstruct the transmitted data bytes within the device's own registers.

In this embodiment only one device, the central control device, transmits the synchronization pattern and initiates a communications sequence. Interrupts and communications directly from one device to another are not supported in the presently described embodiment although a modification of firmware would allow for such support.

In order that the device's microcontroller does not spend too much of its time awaiting a synchronization pattern, the transmission of that pattern is restricted to a window following, but delayed from, the negative-going zero-crossover of the 24 Volt AC waveform. The delay avoids transient electrical artifacts that result from various actions related to the zero-crossings, such as the triggering of triacs. The detection window is wide enough to accommodate the synchronization pattern plus phase shift in the AC waveform. Inductive loads on the system cause a lagging current flow through the resistance of the two-wire network. This in turn causes a phase shift between the high frequency burst pattern and the line frequency AC waveform which increases as the wire length and line resistance increase. It is the drawing of power from the network by the solenoid valves that causes this shift. Thus, as valves are turned on and off the relative timing between the high frequency bursts and the crossover of the AC line frequency changes. Capacitive loads cause a shift in the opposite direction. Consequently, it can be seen that the line frequency AC waveform is a poor timing reference when it comes to locating the bit windows, however, it does work well as an approximate indication of when to begin looking for a more precise timing pattern.

The more precise timing pattern consists of a long burst of sinusoidal energy of the exact frequency of the data bursts. Consequently, it propagates with exactly the same timing as the data bursts and is therefore an excellent timing reference. In the midst of the timing pattern, a 180-degree phase reversal is injected. Signal processing by the microcontroller in each device detects this reversal and uses it as a timing reference for the data bits and bytes that follow.

The central controller initiates a communications sequence consisting of the following elements, with each occurring in a separate negative half-cycle:

1. A transmitted synchronization pattern containing a 180-degree phase reversal followed by a device address within the same negative half-cycle.
2. A device command
3. Data byte 1 to the device
4. Data byte 2 to the device The central controller then enters its receive mode and picks up four bytes from the addressed device as follows:

5. Data byte 1 from the device
6. Data byte 2 from the device
7. Status byte from the device
8. Communications checksum from the device.

Eight contiguous cycles of the line frequency (say, 133 msec at 60 Hz, or 160 msec at 50 Hz) are required for a full communications sequence. The maximum communications rate is at the line frequency, which in the preferred embodiment is 60 bytes per second. Only the addressed device responds to the issued command and returns data. The '0' address causes all devices to execute the command but no data will be returned by any of them.

DETAILED DESCRIPTION

The described system allows a common controlling device to communicate with multiple remote devices over the same wiring that is used to provide power to those devices. In an underground sprinkler irrigation system the controlling device is a proprietary irrigation controller with a two-wire interface. The remote devices may be switches to activate solenoid valves or they may be moisture sensors, temperature sensors, flow meters, pressure meters, rainfall detectors, anemometers or such other devices that may be useful in controlling the application of irrigation water. Other devices such as outdoor lighting for a yard or playing field may be controlled by the described system. Security sensors may also be interrogated and access gates may be controlled. Although the focus of the preferred embodiment as described here is on control of solenoid valves, persons familiar with automation and security systems will readily recognize alternate uses for the described two-wire network, especially such a network that is capable of operating underground and covering long distances.

Figure 1:
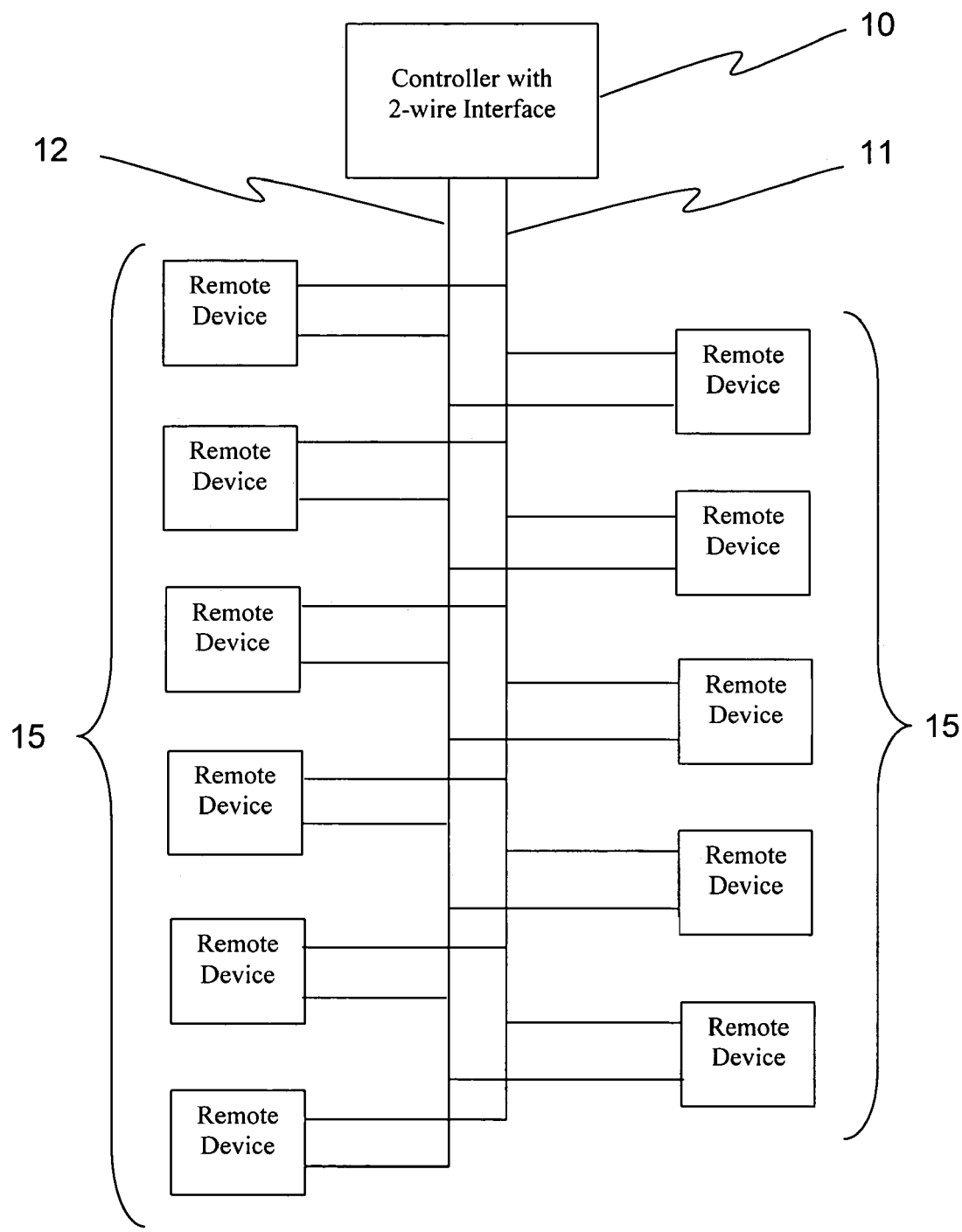
FIG. 1 is a topographical diagram of a typical application using the invention.

FIG. 1 shows the general layout of a two-wire power and communications network. The controller 10 provides 24 Volts AC power on the common conductor 11 and the hot conductor 12. Each remote device 15 on the system connects to the common and hot conductors. The wiring method used by the two conductors in reaching all of the remote devices can take on any of several non-critical connection styles. Wires may run from one device to the next using paired wire, may 'star' from a single node pair or multiple node pairs to all devices or may be configured with one conductor running from device to device and the other as a direct star connection to each individual device. The only requirement is that each remote device must have at least one connection along some path, however complex, back to each of the common and hot terminals at the controller. Redundant connections from the controller to the, remote network are allowed, yielding alternate power and communications paths that will maintain operational integrity of the system in case some wires should become severed or otherwise disconnected, as long as at least one connection remains to each of the common and hot terminals.

The devices on the network in the preferred embodiment are powered by 24 Volts AC at 60 Hz. With minor adjustments to allow for different timings due to nominal power line frequency, other embodiments will accommodate other standard regional power line frequencies, such as 50 Hz. It will be further recognized by those familiar with such matters that other embodiments may be built upon systems ranging, for example, from 12 VAC for low voltage lighting, to 240 VAC appliances. The particular selection of 24 Volts AC at 60 Hz was made because a major function of the described system is to activate 24 Volt AC solenoid valves that control the application of water in the irrigated zones managed by the system. The reliable operation of those valves is critical to the success of the irrigation system. Several manufacturers provide a wide variety of designs of these valves to the industry, but the common standard among them is operation at 24 Volts AC, 60 Hz.

Figure 5:
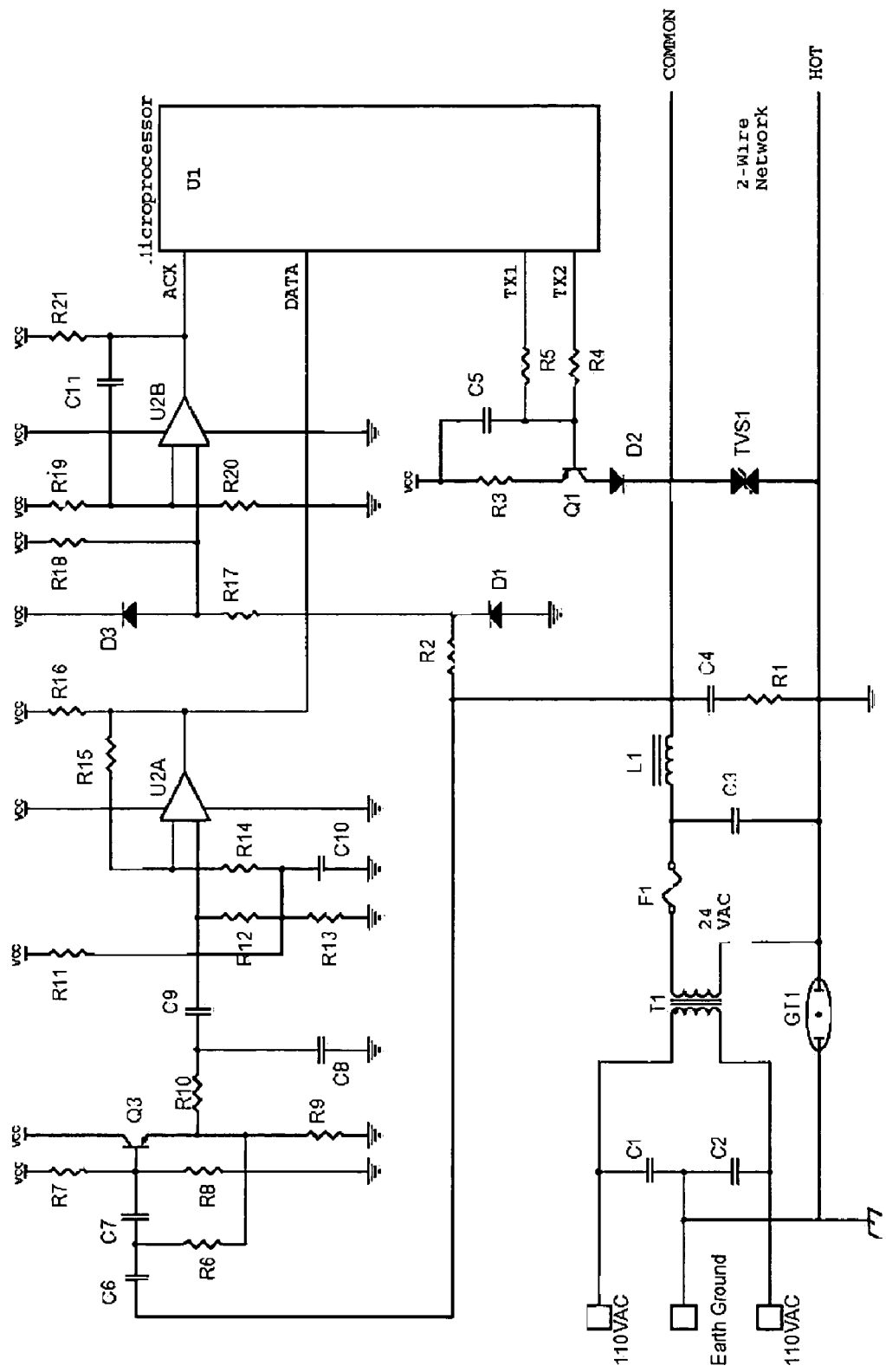
FIG. 5 is a schematic diagram showing how power is applied to the two-wire system, and how data is applied to and retrieved from the network.

Power is applied to the network from a 24 Volt AC transformer through a 5 millihenry inductor, shown as L1 in FIG. 5. The purpose of the inductor is to provide a bi-directional filter to high-frequency energy in the range of the 19.2 kHz modulation that will be used for communication, and to render the power source as a high impedance to 19.2 kHz signals on the two-wire network. In environments where considerable noise in the 19.2 kHz range exists on the power line, additional filtering may be required.

Communications over the network is based upon transmitting and receiving bursts of 19.2 kHz energy. A 19.2 kHz waveform has a period of 52.08 microseconds during which time an electrical signal traveling at the speed of light may propagate to an extent of nearly ten miles. After taking into account the signal reflections caused by loops, multiple paths, uncontrolled reactances and poor terminations within a network, 19.2 kHz modulations can still be reliably broadcast over a mile or more. Another consideration in the selection of 19.2 kHz as a modulation frequency is that, with 320 cycles of 19.2 kHz within a single cycle of 60 Hz power, there is sufficient time available to implement a reliable coding methodology while still achieving a suitable data rate. A sinusoid at 19.2 kHz is developed through division by 1024 of the readily available oscillator frequency of 19.6608 MHz that is used in the preferred embodiment as the master clock to the microcontroller.

One data bit is represented by a transmission of 10 cycles at 19.2 kHz, having a duration of 520.8 microseconds. A frequency discriminating receiver at the other end of the communication link examines the waveform received in the 520.8 microsecond window. If at least 5 full cycles correlate with one another in matching a 19.2 kHz waveform then a '1' has been detected. If fewer than 5 correlating cycles are found, then detection of a '0' is assumed. Sinusoidal bursts were chosen as the signaling means because over networks where reactance is uncontrolled such bursts propagate without distortion, except at the leading and trailing cycles of the burst. Reflections from multiple unterminated network segments also do not distort the center cycles but merely shift their phase as a group and/or modify their amplitude. The microcontroller code that detects the burst is designed to correlate relative cycle-to-cycle timing rather than absolute window-referenced timing. Also the filtered analog waveform is converted to a binary waveform by a comparator before presentation to the microcontroller. Hence phase shift and amplitude modifications to the burst have an insignificant impact on its reliable detection.

Figure 2:
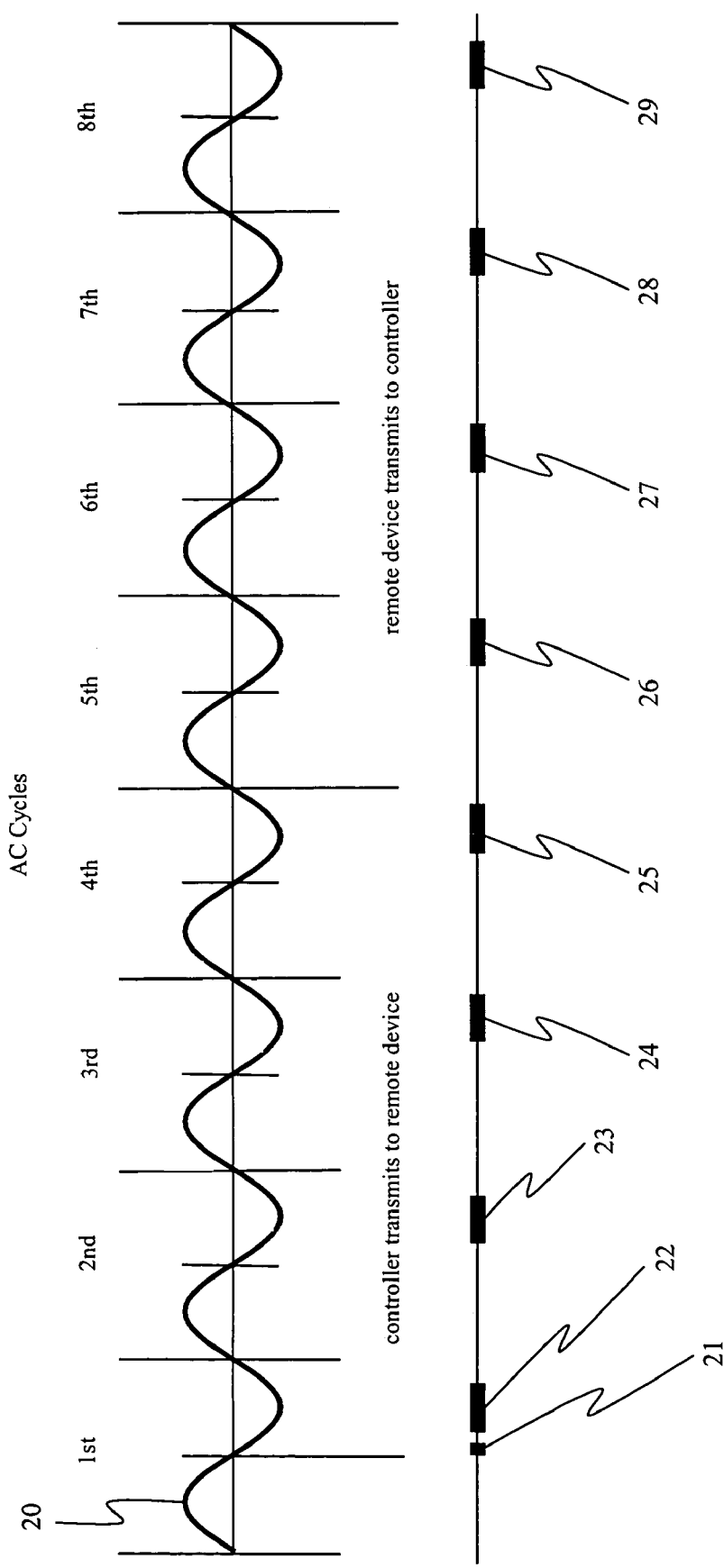
FIG. 2 is a representation of a communications sequence showing the synchronization, transmitted data and received data portions of the sequence.

FIG. 2 is a diagram showing the relative timing of the portions of a communications cycle carried on AC waveform 20 of the power line as implemented in the present invention. A full communications cycle is divided into two portions with the controller transmitting during the first portion and a remote device responding during the second. The controller initiates all communications on the two-wire network. Transmission is allowed only during the negative half-cycle of the 24 Volt AC waveform. Thus, the controller first waits for a negative crossover. As shown in FIG. 5, this crossover is presented to the ACX input of the microcontroller U1 via comparator U2B. At 1016 microseconds after the negative crossover of the AC, the controller begins to transmit a 19.2 kHz sine wave burst having a duration of 20 cycles. This synchronization burst 21 is shown in FIG. 2. A phase reversal during the synchronization burst is used as a timing reference mark to synchronize the remote devices to the subsequent command and data bursts. The reason for using this timing reference mark instead of the AC crossover is that the 60 Hz AC power waveform and the 19.2 kHz signaling frequency do not maintain the same phase relationship throughout the network due to line resistance and switched reactances, such as those due to solenoid valves on the network. The timing must be derived from a signal having the same spectral properties as the data bursts so that the timing relationship between the timing reference mark and the data bursts is subject to the same group delay and is therefore constant throughout the network and is maintained even through the switching of inductive loads.

At precisely 260 microseconds after the phase reversal timing reference mark, the controller begins the transmission of the remote device address 22 of FIG. 2. This 8-bit field identifies the remote unit to which the communication is addressed. If a zero code is transmitted (that is, hexadecimal 00), all remote devices should respond to the subsequent command. Otherwise, only the addressed device will respond. Exactly one full cycle of the power line after the start of the address field, the transmission of the command field begins. This one cycle offset is 16,667 microseconds in a system using 60 Hz AC power. (Those skilled in these matters will recognize the need to adjust this to 20,000 microseconds for a 50 Hz system and to scale other timing values accordingly.) The 8-bit opcode carried in command field 23, defines the operation that the addressed remote device is to perform. Some typical operations are to write to, or read from, a register, or a device pin, controlling a triac or other device that invokes some action.

In the third and fourth negative half-cycles, two data bytes (24 and 25) are transmitted to the remote device. The remote device uses these data bytes according to the previously given command 23.

Between the fourth and fifth power cycles, the remote device performs the action called for by the opcode. Then the remote device responds to the controller with four bytes of data. The timing for the transmission of these bytes continues to refer back to the phase reversal timing reference mark from the first negative half-cycle. The first two returned bytes (26 and 27) are data. Status byte 28 describes the condition of the remote device. Completing the communications sequence is a checksum byte 29 covering all seven of the other transmitted and received bytes.

Figure 3:
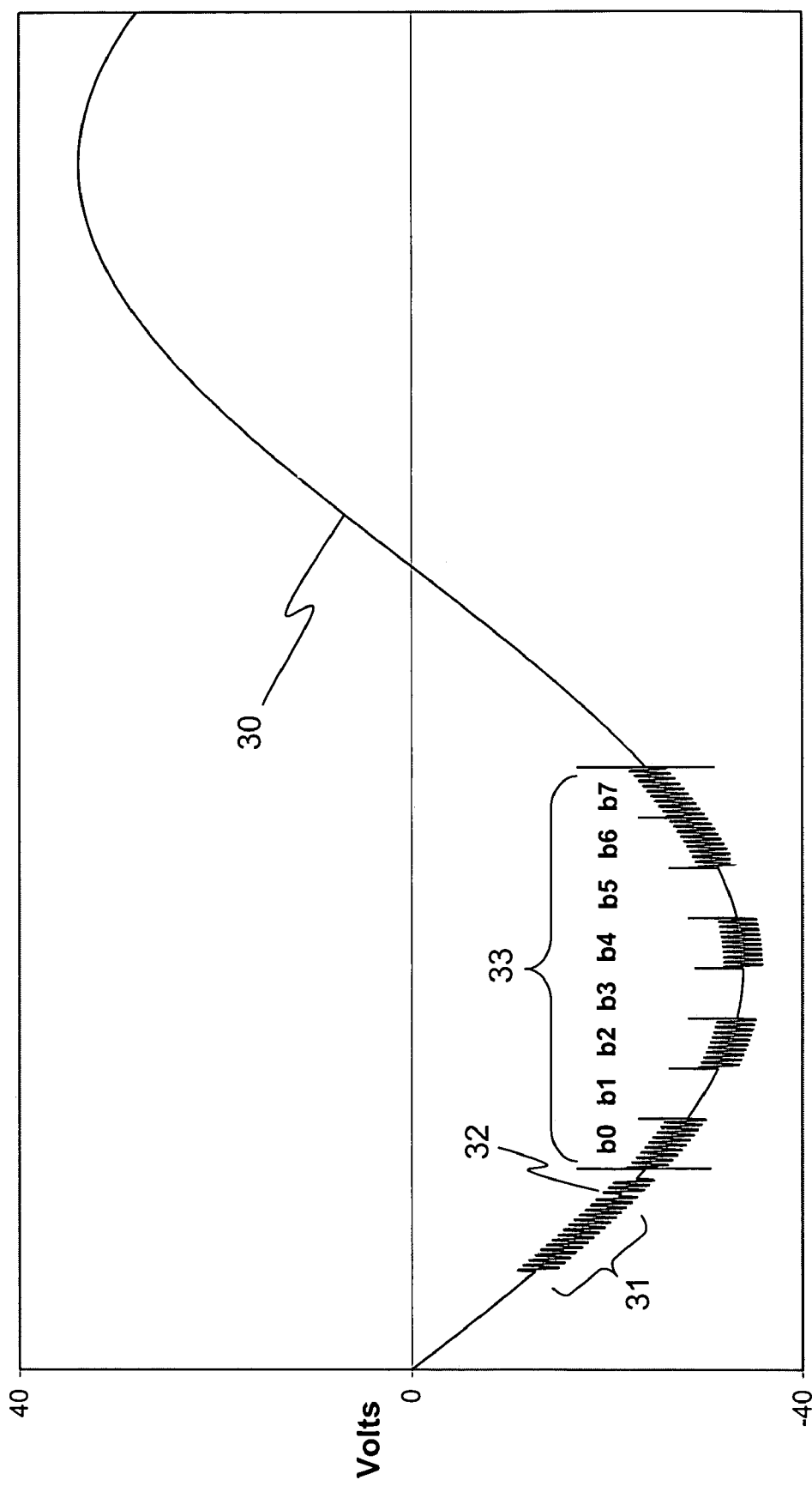
FIG. 3 shows a possible waveform associated with the first negative half-cycle of a communications sequence.

FIG. 3 is a depiction of the information transmitted by the controller in the first negative half-cycle, corresponding to 21 and 22 of FIG. 2. The individual bit locations of the address byte 33 are shown along with the synchronization code (31 with 32) preceding them. The example address shown in the address field is hex D5. The controller transmits this burst of information by injecting a sinusoidal current of 40 ma peak-to-peak (p—p) onto the common wire of the two-wire network as shown in FIG. 5. A tri-state pulse width modulation scheme comprised of microcontroller U1, resistors R3, R4 and R5, PNP transistor Q1, capacitor C5 and diode D2 generates the 19.2 kHz current waveform. This sinusoidal current applied across the 100-ohm terminating resistor R1 superimposes a 4 Volt p—p 19.2 kHz waveform onto the 24 Volt AC 60 Hz waveform during the negative half-cycle.

Phase Lock Process

Figure 4:
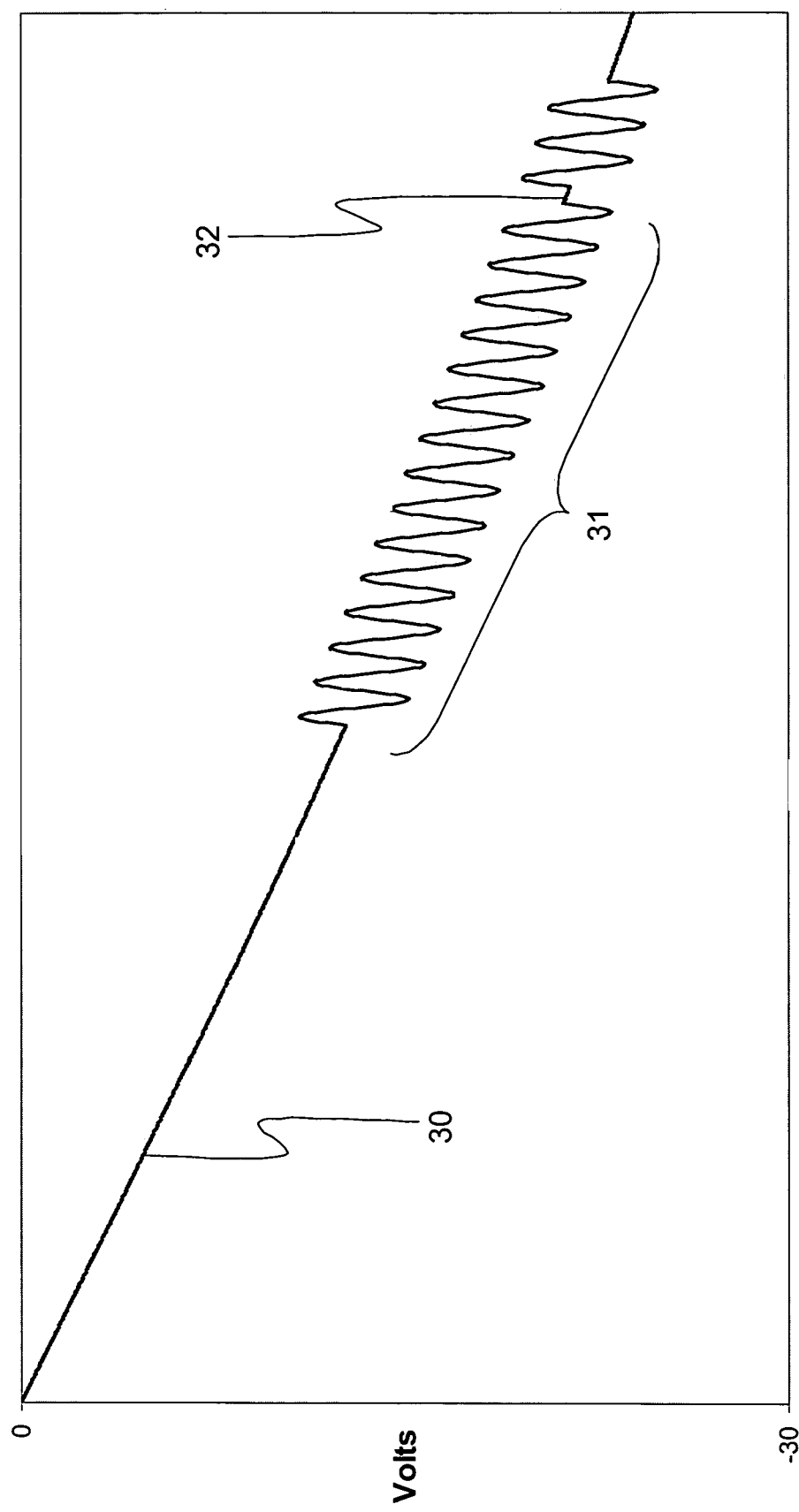
FIG. 4 is an expansion of FIG. 2 showing the details of the timing pattern used to synchronize the controlled devices to the subsequent data patterns.

FIG. 4 is an expansion of the synchronization field of FIG. 3. The synchronization pattern 31 generated by the controller consists of 16 cycles of 19.2 kHz waveform followed by a 180-degree phase shift (the timing reference mark 32) and 3½ more phase-reversed cycles. The first 16 cycles provides the phase lock field and is used by the remote receivers to establish phase synchronization. Each remote device contains a crossover detector, a data receiver and a data transmitter exactly like these same three elements shown for the controller in FIG. 5. The two-wire network data arrives at the receiver of the remote device through C6 (FIG. 5), the first element in an active two-zero high pass filter. The 60 Hz component of the signal appearing on the emitter of Q3 has been attenuated by 80 db. The combination of C9 and R12 provide an additional 40 db of attenuation to 60 Hz, bringing the 24 Volt AC power signal down to around 2.4 micro-Volts rms. Some attenuation to spectral noise above 20 kHz is provided by R10 and C8. Comparator U2A converts the filtered 19.2 kHz sinusoidal bursts to a binary waveform wherein the positive portion of the sinusoid is converted to a '1' level called a '1 chip' and the negative portion of the sinusoid is converted to a '0' level called a '0 chip.'

Starting with a lead of 17 chips (9.56 degrees of the 60 Hz waveform) over the anticipated position, the receiver begins to look for the 19.2 kHz burst. The early start accommodates timing shifts between the 60 Hz waveform and the 19.2 kHz bursts. The receiver continues searching for the phase lock field for a total of 100 chips (56.3 degrees of 60 Hz) before abandoning the search. This sets up a relatively wide window for the receiver to find the synchronization mark.

The receiver uses the capture facility of the PIC16F8XX microcontroller family in the phase lock process. In this facility, Timer 1 is set up as a 16-bit counter that is clocked with every machine cycle. Whenever a transition of chosen polarity occurs on the DATA input pin (the capture trigger pin) the count in Timer 1 is saved and the processor is interrupted.

At the beginning of the phase lock search, the capture trigger (DATA) is set for triggering on the negative transition, the waveform on the system bus having been inverted before arriving at the DATA pin. This means that the first chip in the string of 32 phase lock chips will be ignored. That chip is subject to distortion since it must establish the quiescent conditions in the filters for the subsequent waveform. When the negative edge occurs, the count in Timer 1 is stored in the first of four sixteen-bit registers. When the next transition occurs the Timer 1 count is stored in the second of the four sixteen-bit registers. The process is repeated for the next two samples. After four samples have been stored, the next sample overwrites the first one so that the registers act as a circular buffer containing the time of occurrence of the last four positive transitions.

After the processor stores each sample, it examines the contents of the cycle time registers looking for a 19.2 kHz pattern. The cycle time for 19.2 kHz is 256 of the microcontroller's machine cycles. The criterion used in the search is that four contiguous cycles need to be found in which the overall time for four cycles is within sixteen machine cycles of 1,024, and the timing between consecutive cycles is also within sixteen cycles of 256. This means that four contiguous uniform cycles have been found and the frequency of the four uniform cycles is between 18,905 Hz and 19,505 Hz or 19,200 (+305, −295) Hz. Of the sixteen cycles that would have been transmitted at that frequency, four of them that are contiguous must be found to meet the criterion.

The processor starts at the current pointer location and works backwards through the four registers, subtracting the content of the previous register from the register addressed by the pointer. If the difference is within the range of +/−16 then the pointer is decremented and the process repeats until the fourth difference has been evaluated. Then the difference over the whole four-cycle span is taken and also tested for the same +/−16 machine cycle limit. If any of the five tests fail along the way the pointer is restored, the process is terminated and the processor waits for the next reading. If all five tests pass, then the last sample time is taken as an accurate base for the positive edge of the 19.2 kHz cycle. The center of the positive chip is then 64 cycles later, +/−16 cycles. And each 128 cycles thereafter is the center (+/−16 cycles) of all succeeding chips in the phase lock field and timing mark. The last task is to then use this timing pattern to detect the phase reversal pattern and thus the timing mark.

Timing Pattern Detection

The phase shift in the 19.2 kHz pattern causes a discontinuity in the sinusoidal signal and thus is subject to distortion until the sinusoid is again restored in its new phase. Not only is the single chip delay subject to distortion in the receiver filters, but the succeeding startup of the phase-shifted sinusoid is also distorted. To eliminate the effects of this distortion in detecting the phase reversal, no attempt is made to look for the reversal within the time window of these two distorted chips. Rather the phase shift pattern is eight chips wide with the two center chips regarded as "don't care" while the outer six chips are seen as two strict triples in which the phase is reversed.

The sought after pattern is: 0 1 0 X X 0 1 0, wherein '0' and '1' are definite logic values and 'X' signifies that the signal sample in the corresponding sample window is unimportant.

The reception of this pattern requires that the last three chips of the phase lock field and the second, third and fourth chips of the reversed field be at the senses shown at the center of the chip window. The delay chip and the first chip of the reversed field are ignored and can contain noise and distortion without affecting the synchronization process.

The process for the detection of this pattern is this: After the 19.2 kHz signal has been found and the sample timing is established at the center of the succeeding chips, the DATA pin is sampled with each chip clock (128 cycle spacing of the microcontroller clock). The DATA pin sense is placed into a shift register. After each sample the register content is moved to a working register where it is masked (logically ANDed) with the pattern 11100111 so that only bits 0, 1, 2, 5, 6 and 7 are tested. The result is compared to the pattern hex 42. If a match exists then the last sample was the timing reference mark to within +/−16 machine cycles. The sampling and testing continues until the match is found or until the allowable number of samples has been met. In the latter case the processor is returned to wait for the next negative crossover. If the match is found then the address field sampling starts at 832 machine cycles after the successful sample time. The sampling will start within +/−12.5% of the chip width of the first address chip.

Data Byte Detection

Following the acquisition of phase-lock and the location of the timing reference mark, the receiver is prepared to capture data. These subsequent data bursts are detected using an approach similar to that disclosed for acquiring phase lock. The first byte following the synchronization pattern 21 of FIG. 2 will be the address byte 22 that is expanded as bits b0 through b7 in 33 of FIG. 3. This first byte is transmitted at a precise time relative to the previously transmitted timing mark. The receiving device also uses an internal virtual clock referenced to the timing mark to establish the point in time at which the sampling process will commence to detect the first bit of this first byte. At that point the waveform appearing on the DATA pin is examined in a similar manner as with the detection of the 19.2 kHz phase lock signal. If 12 or more chips are found that meet the criterion of 19.2 kHz periodicity, then a '1' has been detected, otherwise, a '0' has been detected. The number of chips transmitted is 20. In this case the qualifying chips need not be contiguous. They may be interspersed with non-aligned noise provided they align with each other with 19.2 kHz periodicity. The address field, command field and data fields are each decoded in this manner, with the processing of each bit window referenced to the previously detected timing mark.

The addressed receiver decodes the command from its controller at segment 23, takes in the data from segments 24 and 25 and acts on them as instructed. It then returns two appropriate data bytes in segments 26 and 27, followed by a byte to indicate its self-detected status 28. The receiver then appends a calculated checksum 29 to cover the previous seven bytes, the first four of which were received from its controller and the latter three having been generated within the receiver.

Although the described embodiment of the present invention refers specifically to networks operating at 24 VAC 60 Hz, it must be appreciated that the techniques shown may be readily applied to power lines of other voltages. Those skilled in the pertinent field will recognize applications ranging from low voltage lighting systems operating at 12 VAC or even less, to the 240 VAC more commonly found in settings where commercial appliances are to be controlled.

Having successfully targeted the outdoor environment, which is extremely difficult to control, and having accommodated subterranean conditions, the present invention may be easily adapted to networks of power lines surrounded by most any media, above or below ground or water.

The description of a particular embodiment of the invention is not intended to be exhaustive or to limit the invention to the form disclosed. Those skilled in the relevant arts will recognize that the components specifically referenced here will enable such a person to construct other systems that are similar to those disclosed here to provide further embodiments more readily applicable to specific environments and purposes. While a specific embodiment of the invention has been described, various modifications are possible within the scope of the invention, as those possessing such skills will recognize. The scope of the invention is to be determined by the appended claims which are intended to cover any modifications falling within the spirit of the invention.

What is claimed is:

1. An apparatus which integrates power and bi-directional data transmission in order to control the operation of and monitor information from various electrical equipment modules in a control system comprising:
   a. two conductors of alternating current electrical power including
      a first conductor acting as a voltage supply line; and
      a second conductor, the second conductor capable of being at once
         a return conductor for power distribution; and
         a return conductor for asynchronous data transmission;
   b. at least one controller electrically connected to said two conductors for the generation and transmission of a data signal; and
   c. at least one addressable controlled device having a device address associated therewith, the controlled device being electrically connected to said two conductors and capable of receiving said data signal generated by said controller;
   wherein said data signal is comprised of bursts of sinusoidal waves superimposed onto said alternating current electrical power transmitted on said two conductors, said sinusoidal waves being of uniform frequency, said uniform frequency being a higher frequency than the frequency of said alternating current electrical power, said superimposition occurring within a single half-cycle of selected polarity of said alternating current electrical power.

2. The apparatus of claim 1 wherein a first type of said bursts of sinusoidal waves is a synchronization pattern.

3. The apparatus of claim 1 wherein a second type of said bursts of sinusoidal waves represents data bits.

4. The apparatus of claim 1 wherein said alternating current electrical power is of a known frequency and has zero crossings.

5. The apparatus of claim 4 wherein said superimposition of bursts of sinusoidal waves is referenced to one of said zero crossings of said alternating current electrical power as a first reference.

6. The apparatus of claim 5 wherein said bursts of sinusoidal waves include a first burst, said first burst is of a first type of said bursts of sinusoidal waves, said first type is a synchronization pattern, said synchronization pattern contains a second reference following said first reference, said second reference is a phase reversal of said sinusoidal waves.

7. The apparatus of claim 6 wherein said bursts of sinusoidal waves may optionally include one or more subsequent bursts of a second type, said second type of said bursts represents a data bit.

8. The apparatus of claim 7 wherein a first of two possible binary states of said data bit is indicated by the presence of a minimum number of cycles of said sinusoidal waves within a time slot, and a second of the two possible binary states of said data bit is indicated by the absence of said minimum number of cycles of said sinusoidal waves within said time slot, said time slot is referenced to, and offset in time from, said second reference.

9. The apparatus of claim 8 wherein a set of consecutive data bits forms a data byte, said data byte is coded in a set of consecutive time slots, each time slot of said set of consecutive time slots sequentially represents a next one of said set of consecutive data bits.

10. The apparatus of claim 9 wherein no more than one of said data byte is coded within an instance of said single half-cycle of selected polarity of said alternating current electrical power.

11. The apparatus of claim 9 wherein said data signal includes a multiplicity of communications sequences, each communications sequence comprises exactly one of said synchronization pattern followed by a set of coded data bytes.

12. The apparatus of claim 11 wherein said set of coded data bytes within said communications sequence comprises:
   a. a first byte, said first byte follows said synchronization pattern and is precisely delayed a first amount of time from said second reference and occurs within a first of a set of said single half-cycle of selected polarity of said alternating current electrical power, said first byte is an address;
   b. a second byte, said second byte is precisely delayed a second amount of time from said second reference and occurs within a second of a set of said single half-cycles, said second byte is a command;
   c. third and fourth bytes, said third and fourth bytes are precisely delayed a third and fourth amount of time from said second reference and occur within third and fourth of a set of said single half-cycles, said third and fourth bytes are data associated with said command;
   d. fifth and sixth bytes, said fifth and sixth bytes are precisely delayed a fifth and sixth amount of time from said second reference and occur within fifth and sixth of a set of said single half-cycles, said fifth and sixth bytes are response to said command;
   e. a seventh byte, said seventh byte is precisely delayed a seventh amount of time from said second reference and occurs within a seventh of a set of said single half-cycles, said seventh byte is status; and
   f. an eighth byte, said eighth byte is precisely delayed an eighth amount of time from said second reference and occurs within an eighth of a set of said single half-cycles, said eighth byte is a checksum over all of said first through seventh bytes.

13. The apparatus of claim 12 wherein said synchronization pattern and said first through fourth bytes are generated and transmitted by a first of said at least one controller and said fifth through eighth bytes are generated and transmitted by a selected device of said at least one addressable controlled device, said selected device having been selected by a match of address transmitted in said first byte of said set of coded data bytes within said communications sequence.

14. A communications network comprised of the apparatus of claim 12 wherein said synchronization pattern and said first through fourth bytes are generated and transmitted by a first of said at least one controller, and said first byte, being said address, contains the zero code, and all of said controlled devices on said communications network respond to said command and to said data associated with said command transmitted in said second through fourth bytes, but none of said controlled devices transmits any response during the time slots designated for said fifth through eighth bytes of said communications sequence.

15. The communications network of claim 14 wherein at least 255 instances of said at least one addressable controlled device may be independently controlled by unique addresses transmitted in said first byte of said communications sequence.

16. The apparatus of claim 1 wherein said alternating current electrical power has a voltage in the range of 10 VAC to 30 VAC.

17. The apparatus of claim 1 wherein said alternating current electrical power has a voltage that is nominally 24 VAC.

18. The apparatus of claim 1 wherein said alternating current electrical power has a voltage in the range of 100 VAC to 130 VAC.

19. The apparatus of claim 1 wherein said alternating current electrical power has a voltage in the range of 200 VAC to 240 VAC.

20. The apparatus of claim 1 wherein said alternating current electrical power has a frequency that is nominally 50 Hz.

21. The apparatus of claim 1 wherein said alternating current electrical power has a frequency that is nominally 60 Hz.

22. The apparatus of claim 1 wherein said sinusoidal waves have a frequency that is in the range of 1 kHz to 50 kHz.

23. The apparatus of claim 1 wherein said sinusoidal waves have a frequency that is nominally 19.2 kHz.

24. The apparatus of claim 1 wherein said electrical equipment modules include solenoid valves for an irrigation system.

25. The apparatus of claim 1 wherein said electrical equipment modules include instrumentation for a deep earth well.

26. The apparatus of claim 1 wherein said electrical equipment modules include sensors of soil, water or weather conditions, said sensors being capable of sensing one or more of soil moisture, soil temperature, soil conductivity, soil acidity, soil permeability, water flow, water pressure, air temperature, wind speed, humidity, and incident solar radiation.

27. The apparatus of claim 1 wherein said electrical equipment modules include sensors for use in a security system, said sensors being capable of sensing one or more of motion, temperature, and the presence or depth of surface water.

28. The apparatus of claim 1 wherein said electrical equipment modules include controls for outdoor lighting.

29. The apparatus of claim 1 wherein said electrical equipment modules include controls for gates or other means of controlling access to an area.

30. A method of transmitting data by a controller on a two-wire network carrying alternating current electrical power, said method comprising within said controller device the steps of:
   a. detecting a zero-crossing of said alternating current electrical power;
   b. delaying a first delay time after said zero-crossing;
   c. superimposing a modulation frequency onto said alternating current electrical power;
   d. introducing a 180-degree phase shift into said modulation frequency after a particular quantity of cycles of said modulation frequency, said phase shift to be used as a timing reference, and continuing said modulation frequency for a total quantity of synchronization cycles of said modulation frequency; and
   e. transmitting a set of data bytes by further superimposition of said modulation frequency onto said alternating current electrical power, each bit of each byte of said set of data bytes being assigned to a corresponding bit-wise time slot from a set of bit-wise time slots, each said bit-wise time slot being referenced in time from said timing reference, each '1' bit being encoded by the presence of a data quantity of cycles of said modulation frequency during said corresponding bit-wise time slot, and each '0' bit being encoded as the absence of said data quantity of cycles of said modulation frequency during said corresponding bit-wise time slot.

31. The method of claim 30 for transmitting data by a controller on a two-wire network, wherein:
   a. said bit-wise time slots are clustered into a set of byte-wise time slots with no delays between said bit-wise time slots within each of said byte-wise time slots;
   b. each of said byte-wise time slots is separated in time from adjacent byte-wise time slots so that no more than one of said byte-wise time slots occurs within any half-cycle of said alternating current electrical power; and
   c. said byte-wise time slots are restricted to occur during allowed half-cycles of said alternating current electrical power where said allowed half-cycles have a given polarity of said alternating current electrical power and alternate half-cycles, having polarity opposite of said given polarity, are disallowed.

32. The method of claim 31 for transmitting data by a controller on a two-wire network, wherein said set of data bytes are transmitted in said set of byte-wise time slots, and said set of byte-wise time slots comprises:
   a. a first byte-wise time slot, a first data byte of said set of data bytes is transmitted by a controller in said first byte-wise time slot, said first byte-wise time slot follows said total quantity of synchronization cycles, both of said total quantity of synchronization cycles and said first byte-wise time slot occur in a first of said allowed half-cycles, said first byte is an address;
   b. a second byte-wise time slot, a second data byte is transmitted by said controller in said second byte-wise time slot, said second byte-wise time slot occurs within the next allowed half-cycle following said first byte-wise time slot, said second data byte is a command;
   c. third and fourth byte-wise time slots, said third and fourth data bytes are transmitted by said controller in third and fourth byte-wise time slots, said third and fourth byte-wise time slots occur within the next two allowed half-cycles following said second byte-wise time slot, said third and fourth data bytes are data associated with said command; and
   d. four reserved byte-wise time slots, said reserved byte-wise time slots allow said controller to receive data bytes transmitted by a selected controlled device.

33. The method of claim 30 for transmitting data by a controller on a two-wire network, wherein said modulation frequency is in the range of 1 kHz to 50 kHz.

34. The method of claim 30 for transmitting data by a controller on a two-wire network, wherein said modulation frequency is nominally 19.2 kHz.

35. The method of claim 30 for transmitting data by a controller on a two-wire network, wherein said alternating current electrical power has a voltage in the range of 10 VAC to 30 VAC.

36. The method of claim 30 for transmitting data by a controller on a two-wire network, wherein said alternating current electrical power has a voltage that is nominally 24 VAC.

37. The method of claim 30 for transmitting data by a controller on a two-wire network, wherein said alternating current electrical power has a voltage in the range of 100 VAC to 130 VAC.

38. The method of claim 30 for transmitting data by a controller on a two-wire network, wherein said alternating current electrical power has a voltage in the range of 200 VAC to 240 VAC.

39. The method of claim 30 for transmitting data by a controller on a two-wire network, wherein said alternating current electrical power has a frequency that is nominally 50 Hz.

40. The method of claim 30 for transmitting data by a controller on a two-wire network, wherein said alternating current electrical power has a frequency that is nominally 60 Hz.

41. The method of claim 30 for transmitting data by a controller on a two-wire network, wherein said controller controls an irrigation system.

42. The method of claim 30 for transmitting data by a controller on a two-wire network, wherein said controller controls one or more sensors of soil, water or weather conditions, said sensors being capable of sensing one or more of soil moisture, soil temperature, soil conductivity, soil acidity, soil permeability, water flow, water pressure, air temperature, wind speed, humidity, and incident solar radiation.

43. The method of claim 30 for transmitting data by a controller on a two-wire network, wherein said controller controls a security system.

44. The method of claim 30 for transmitting data by a controller on a two-wire network, wherein said controller controls a lighting system.

45. The method of claim 30 for transmitting data by a controller on a two-wire network, wherein said controller controls instrumentation in a deep earth well.

46. A method of receiving data by an addressable controlled device on a two-wire network carrying alternating current electrical power, said method being implemented within said addressable controlled device and comprising the steps of:
   a. finding a zero-crossing of said alternating current electrical power;
   b. delaying a first delay time after said zero-crossing;
   c. searching for a signal frequency within a desired frequency band on said alternating current electrical power while measuring a first elapsed time, and returning to said detecting step if said first elapsed time reaches a first maximum elapsed time before said signal frequency is recognized;
   d. detecting a phase reversal of said signal frequency while counting cycles of said signal frequency, and returning to said finding step if said counting reaches a first maximum count;
   e. operating a virtual clock generator at said signal frequency, said virtual clock generator is synchronized to said phase reversal and starts a received data timer upon said detecting of said phase reversal;
   f. establishing a set of time windows based upon said received data timer wherein each received data bit belonging to a set of received data bits is expected to fall within a corresponding time window within said set of time windows;
   g. counting cycles of said signal frequency within each of said time windows; and
   h. assigning a logical data bit value of '1' to said received data bits where said step of counting cycles yields at least a required minimum data count of cycles during said corresponding time window, and assigning a logical data bit value of '0' to said received data bits where said step of counting cycles fails to reach said required minimum data count of cycles during said corresponding time window.

47. The method of claim 46 for receiving data by an addressable controlled device on a two-wire network, wherein a set of received data bytes is constructed by grouping of said received data bits into said set of received data bytes.

48. The method of claim 47 for receiving data by an addressable controlled device on a two-wire network, wherein said set of time windows established by said step of establishing a set of time windows includes a sufficient quantity of said time windows to accommodate construction of at least eight of said received data bytes.

49. The method of claim 48 for receiving data by an addressable controlled device on a two-wire network, wherein said method further comprises the steps of:
   a. comparing a first received data byte of said set of received data bytes to a pre-assigned address of said addressable controlled device, said first received data byte is taken as an address byte;
   b. ignoring said set of received data bytes if said comparing step is not a match and said first received data byte is not zero;
   c. taking a first action by said addressable controlled device in accord with a first pre-programmed function when said first received data byte is zero, said first action may optionally depend upon a second received data byte, a third received data byte and a fourth received data byte, said first action will not cause any data to be transmitted by said addressable controlled device;
   d. taking a second action by said addressable controlled device when said first received data byte matches said pre-assigned address of said addressable controlled device as tested in said comparing step, said second action being selected from a set of pre-programmed functions determined by a second received data byte, said second received data byte taken as a command, optionally using a third received data byte and a fourth received data byte to modify said second action;
   e. transmitting onto said two-wire network a fifth data byte and a sixth data byte, said fifth data byte and said sixth data byte being composed in accordance with said second action, and said fifth data byte and said sixth data byte being transmitted during those time windows within said set of time windows that correspond to a fifth data byte and a sixth data byte of said at least eight of said received data bytes;
   f. reporting onto said two-wire network a seventh data byte, said seventh data byte being composed to report status of said addressable controlled device following said second action, and said seventh data byte being reported during that time window within said set of time windows that corresponds to a seventh data byte of said at least eight of said received data bytes;

g. confirming onto said two-wire network an eighth data byte, said eighth data byte being composed as a checksum of said first through seventh data bytes, and said eighth data byte being confirmed onto said two-wire network during that time window within said set of time windows that corresponds to an eighth data byte of said at least eight of said received data bytes; and h. said steps of transmitting, reporting and confirming being accomplished by superimposing onto said two-wire network a quantity of full cycles of said signal frequency to fill each of said time windows where a '1' bit is to be encoded, and inhibiting modulation during those of said time windows in which a '0' bit is to be encoded.

50. The method of claim 46 for receiving data by an addressable controlled device on a two-wire network, wherein said signal frequency is in the range of 1 kHz to 50 kHz.

51. The method of claim 46 for receiving data by an addressable controlled device on a two-wire network, wherein said signal frequency is nominally 19.2 kHz.

52. The method of claim 46 for receiving data by an addressable controlled device on a two-wire network, wherein said alternating current electrical power has a voltage in the range of 10 VAC to 30 VAC.

53. The method of claim 46 for receiving data by an addressable controlled device on a two-wire network, wherein said alternating current electrical power has a voltage that is nominally 24 VAC.

54. The method of claim 46 for receiving data by an addressable controlled device on a two-wire network, wherein said alternating current electrical power has a voltage in the range of 100 VAC to 130 VAC.

55. The method of claim 46 for receiving data by an addressable controlled device on a two-wire network, wherein said alternating current electrical power has a voltage in the range of 200 VAC to 240 VAC.

56. The method of claim 46 for receiving data by an addressable controlled device on a two-wire network, wherein said alternating current electrical power has a frequency that is nominally 50 Hz.

57. The method of claim 46 for receiving data by an addressable controlled device on a two-wire network, wherein said alternating current electrical power has a frequency that is nominally 60 Hz.

58. The method of claim 46 for receiving data by an addressable controlled device on a two-wire network, wherein said addressable controlled device is a solenoid valve in an irrigation system.

59. The method of claim 46 for receiving data by an addressable controlled device on a two-wire network, wherein said addressable controlled device is a sensor of soil, water or weather conditions, said sensor being capable of sensing one or more of soil moisture, soil temperature, soil conductivity, soil acidity, soil permeability, water flow, water pressure, air temperature, wind speed, humidity, and incident solar radiation.

60. The method of claim 46 for receiving data by an addressable controlled device on a two-wire network, wherein said addressable controlled device is a sensor for use in a security system, said sensor being capable of sensing one or more of motion, temperature, and the presence or depth of surface water.

61. The method of claim 46 for receiving data by an addressable controlled device on a two-wire network, wherein said addressable controlled device is a lamp control.

62. The method of claim 46 for receiving data by an addressable controlled device on a two-wire network, wherein said addressable controlled device controls a gate or other means of restricting access to an area.

63. The method of claim 46 for receiving data by an addressable controlled device on a two-wire network, wherein said addressable controlled device is instrumentation in a deep earth well.

* * * * *